(12) United States Patent
Li et al.

(10) Patent No.: US 12,667,647 B2
(45) Date of Patent: Jun. 30, 2026

(54) SCAFFOLD COMPOSITE, AND PREPARATION METHOD AND USE THEREOF

(71) Applicant: Kunming University of Science and Technology, Kunming City (CN)

(72) Inventors: Weichao Li, Kunming City (CN); Hongran Ge, Kunming City (CN); Yuncheng Bai, Kunming City (CN); Yayu Zhao, Kunming City (CN); Wen Lei, Kunming City (CN); Chunyan Shen, Kunming City (CN)

(73) Assignee: Kunming University of Science and Technology, Kunming City (CN)

( * ) Notice: Subject to any disclaimer, the term of this patent is extended or adjusted under 35 U.S.C. 154(b) by 0 days.

(21) Appl. No.: 19/230,548

(22) Filed: Jun. 6, 2025

(65) Prior Publication Data

US 2026/0077107 A1 Mar. 19, 2026

(30) Foreign Application Priority Data

Sep. 19, 2024 (CN) .......................... 202411310949.1

(51) Int. Cl.
*A61L 27/44* (2006.01)

(52) U.S. Cl.
CPC .................................. *A61L 27/443* (2013.01)

(58) Field of Classification Search
None
See application file for complete search history.

(56) References Cited

FOREIGN PATENT DOCUMENTS

CN 108704142 A * 10/2018 ............. A61K 47/36

OTHER PUBLICATIONS

Casasola et al. Polymer 2014 55:4728-4737 (Year: 2014).*
Paredes et al. Langmuir 2008 24(19):10560-10564 (Year: 2008).*
Chen et al. ACS Applied Materials and Interfaces 2017 9:4015-4023 (Year: 2017).*
Bayer Materials 2017 10(748):1-33 (Year: 2017).*
Li et al. Journal of Applied Polymer Science 2023 140(e53477):1-22 (Year: 2023).*
Sánchez-Rodríguez et al. Polymers 2021 13(655):1-15 (Year: 2021).*
Belaid et al. Materials Science & Engineering C 110 (2020) 110595:1-10 (Year: 2020).*
Kim et al. Journal of Biosystems Engineering 2019 44:120-127 (Year: 2019).*
Kotsilkova et al. Coatings 2019 9(359):1-14 (Year: 2019).*
Wang et al. Materials Science & Engineering C 2021 118(111457):1-9 (Year: 2021).*
Zennaki et al. Journal of Applied Polymer Science 2022 139(e53095):1-12 (Year: 2022).*
Arriagada et al. Journal of Biomedical Materials Research 2018 106A(4): 1051-1060 (Year: 2018).*

* cited by examiner

Primary Examiner — Melissa S Mercier
Assistant Examiner — Caralynne E Helm
(74) Attorney, Agent, or Firm — Woodard, Emhardt, Henry, Reeves & Wagner, LLP

(57) ABSTRACT

A scaffold composite, and a preparation method and use thereof are provided. The preparation method includes: mixing a graphene oxide (GO) dispersion and a polylactic acid (PLA) dispersion, and subjecting a resulting mixed solution to curing and melt extrusion in sequence to obtain a 3-dimensional (3D)-printable GO/PLA composite wire; subjecting the 3D-printable GO/PLA composite wire to 3D printing to obtain a scaffold; and annealing the scaffold to obtain the scaffold composite.

10 Claims, No Drawings

SCAFFOLD COMPOSITE, AND PREPARATION METHOD AND USE THEREOF

CROSS REFERENCE TO RELATED APPLICATION

This patent application claims the benefit and priority of Chinese Patent Application No. 202411310949.1 filed with the China National Intellectual Property Administration on Sep. 19, 2024, and entitled with "SCAFFOLD COMPOSITE, AND PREPARATION METHOD AND USE THEREOF", the disclosure of which is incorporated by reference herein in its entirety as part of the present application.

TECHNICAL FIELD

The present disclosure relates to the technical field of medical implant materials, and in particular to a scaffold composite, and a preparation method and use thereof.

BACKGROUND

Spinal scaffolds are commonly used implants in spinal surgeries. Traditional scaffold materials primarily include titanium alloys and polyetheretherketone (PEEK). However, although these materials exhibit the desired mechanical properties, their biocompatibility and osseointegration ability require further improvement. In recent years, graphene has attracted much attention in the biomedical field due to its excellent mechanical strength, electrical conductivity, and antibacterial properties. However, graphene is difficult to process and shape, and may cause certain cytotoxic effects.

SUMMARY

Objects of the present disclosure are to provide a scaffold composite, and a preparation method and use thereof. The scaffold composite prepared by the preparation method not only exhibits no obvious toxicity to osteoblasts, but also can promote cell proliferation and differentiation. Furthermore, the scaffold composite exhibits a strong ability to induce the formation of new bone, and the osseointegration is more rapid and solid.

To achieve the above objects, the present disclosure provides the following technical solutions:

The present disclosure provides a method for preparing a scaffold composite, including:

mixing a graphene oxide (GO) dispersion and a polylactic acid (PLA) dispersion, and subjecting a resulting mixed solution to curing and melt extrusion in sequence to obtain a 3-dimensional (3D)-printable GO/PLA composite wire;

subjecting the 3D-printable GO/PLA composite wire to 3D printing to obtain a scaffold; and annealing the scaffold to obtain the scaffold composite.

In some embodiments, a solvent in the GO dispersion and a solvent in the PLA dispersion include independently one or more selected from the group consisting of difluoromethane, fluorobenzene, N,N-dimethylacetamide (DMAc), and N,N-dimethylformamide (DMF).

In some embodiments, the mixing is conducted under stirring at a temperature of 28° C. to 35° C. for 40 min to 80 min; and the PLA dispersion is prepared by mixing PLA with an organic solvent at a temperature of 28° C. to 35° C. for 90 min to 180 min.

In some embodiments, the curing is conducted by vacuum drying; and the vacuum drying is conducted at a temperature of 50° C. to 70° C. for 24 h.

In some embodiments, the melt extrusion is conducted at a die temperature of 190° C. to 210° C. and a screw speed of 12 r/min to 17 r/min.

In some embodiments, a mass ratio of GO to PLA in the 3D-printable GO/PLA composite wire is in a range of 0.001:1 to 0.0025:1.

In some embodiments, the annealing is conducted in an oven; and the annealing is conducted at an oven temperature of 100° C. to 140° C. for 30 min to 90 min.

The present disclosure further provides a scaffold composite prepared by the preparation method as described above.

The present disclosure further provides use of the scaffold composite as described above in preparation of a medical implant material.

In some embodiments, the medical implant material is a spinal scaffold material.

A method for preparing a scaffold composite is provided, including: mixing a graphene oxide (GO) dispersion and a polylactic acid (PLA) dispersion, and subjecting a resulting mixed solution to curing and melt extrusion in sequence to obtain a 3D-printable GO/PLA composite wire; subjecting the 3D-printable GO/PLA composite wire to 3D printing to obtain a scaffold; and annealing the scaffold to obtain the scaffold composite. GO, as a nanomaterial, has a large specific surface area and excellent electron transport properties, which facilitate the adhesion and growth of osteoblasts while enhancing the activity of osteoblasts and the formation processes of bone through the regulation of cell signaling pathways. PLA can partially encapsulate and isolate graphene nanosheets as a matrix, and the composite formed by PLA and GO also creates an interfacial barrier that reduces direct contact and influence on cells, thereby reducing cytotoxicity. In vitro cell experiments show that the scaffold composite of the present disclosure not only exhibits no obvious toxicity to osteoblasts but also can promote cell proliferation and differentiation. Animal implantation experiments show that the scaffold composite exhibits a strong ability to induce the formation of new bone, and the osseointegration is more rapid and solid. The scaffold composite has an elastic modulus of 3 GPa to 5 GPa, which is close to cortical bone, an electrical conductivity of 10 S/m to 100 S/m, which facilitates neural electrical signal transmission, and an antibacterial rate of over 99% against common pathogenic bacteria such as *Staphylococcus aureus* and *Escherichia coli*.

Compared with the prior art, some embodiments of the present disclosure have the following beneficial effects:

1) GO significantly enhances the mechanical strength of the PLA matrix, making it closer to natural bone tissue;

2) GO imparts superior electrical conductivity to the composite, which is beneficial for electrophysiological coupling between the scaffold and the host bone;

3) the unique antibacterial mechanism of GO effectively prevents scaffold-associated infections; and 4) the 3D printing process enables precisely controllable fabrication with a high degree of personalization.

DETAILED DESCRIPTION OF THE EMBODIMENTS

The present disclosure provides a method for preparing a scaffold composite, including the following steps:

mixing a graphene oxide (GO) dispersion and a polylactic acid (PLA) dispersion, and subjecting a resulting mixed solution to curing and melt extrusion in sequence to obtain a 3D-printable GO/PLA composite wire;

subjecting the 3D-printable GO/PLA composite wire to 3D printing to obtain a scaffold; and annealing the scaffold to obtain the scaffold composite.

In the present disclosure, unless otherwise specified, all raw materials for preparation are commercially available products well known to those skilled in the art.

In the present disclosure, a GO dispersion and a PLA dispersion are mixed, and a resulting mixed solution is subjected to curing and melt extrusion in sequence to obtain a 3D-printable GO/PLA composite wire.

In some embodiments of the present disclosure, GO in the GO dispersion has a mass concentration of 0.1 wt % to 1.2 wt %, preferably 0.4 wt % to 1.1 wt %, and more preferably 0.7 wt % to 1.0 wt %. In an embodiment of the present disclosure, the GO in the GO dispersion has a mass concentration of 0.131 wt %, 0.113 wt %, or 0.165 wt %. In some embodiments of the present disclosure, the GO dispersion is prepared by a process including: mixing GO with an organic solvent to obtain the GO dispersion. In some embodiments of the present disclosure, the GO dispersion is prepared by an improved Hummers method. There is no special limitation on the preparation process of the improved Hummers method, which can be conducted by the preparation process well known to those skilled in the art. In some embodiments of the present disclosure, the organic solvent includes one or more selected from the group consisting of difluoromethane, fluorobenzene, DMAc, and DMF, preferably DMF. Under the condition that the organic solvent includes two or more of the above specific options, there is no special limitation on the ratio of the above specific substances, which can be mixed in any ratio. In some embodiments of the present disclosure, the mixing is conducted under an ultrasonic treatment, and the ultrasonic treatment is conducted at a frequency of 40 kHz; and the ultrasonic treatment is conducted for 30 min to 180 min, preferably 60 min to 150 min, and more preferably 110 min to 130 min. In an embodiment of the present disclosure, the ultrasonic treatment is conducted at a frequency of 40 kHz; and the ultrasonic treatment is conducted for 120 min.

In some embodiments of the present disclosure, the PLA dispersion has a mass concentration of 1 wt % to 6 wt %, preferably 2 wt % to 5 wt %, and more preferably 3 wt % to 4 wt %. In an embodiment of the present disclosure, the PLA dispersion may have a mass concentration of 3.915 wt %. In some embodiments of the present disclosure, the PLA dispersion is prepared by a process including: mixing PLA with an organic solvent to obtain the PLA dispersion. In some embodiments of the present disclosure, the organic solvent includes one or more selected from the group consisting of difluoromethane, fluorobenzene, DMAc, and DMF, preferably DMF. Under the condition that the organic solvent includes two or more of the above specific options, there is no special limitation on the ratio of the above specific substances, which can be mixed in any ratio. In some embodiments of the present disclosure, the mixing is conducted under stirring, the stirring is conducted at a temperature of 28° C. to 35° C., preferably 29° C. to 34° C., and more preferably 30° C. to 33° C.; and the stirring is conducted for 90 min to 180 min, preferably 100 min to 150 min, and more preferably 110 min to 125 min. In an embodiment of the present disclosure, the stirring is conducted at 30° C.; and the stirring is conducted for 120 min.

In some embodiments of the present disclosure, the mixing of the GO dispersion and the PLA dispersion is conducted by a process including: slowly adding the GO dispersion into the PLA dispersion while stirring, and continuing to stir after the GO dispersion is completely added. In some embodiments of the present disclosure, the GO dispersion is added at a speed of 1 mL/min to 8 mL/min, preferably 2 mL/min to 6 mL/min, and more preferably 3 mL/min to 4 mL/min. In an embodiment of the present disclosure, the GO dispersion is added at a speed of 4 mL/min. In some embodiments of the present disclosure, the stirring is conducted at a temperature of 28° C. to 35° C., and preferably 30° C. to 32° C.; and the stirring is conducted for 40 min to 80 min, and preferably 50 min to 60 min. In an embodiment of the present disclosure, the stirring is conducted at 30° C., and the stirring is conducted for 60 min.

In some embodiments of the present disclosure, the curing is conducted by vacuum drying; the vacuum drying is conducted at a temperature of 50° C. to 70° C., preferably 55° C. to 65° C., and more preferably 58° C. to 62° C.; and the vacuum drying is conducted for 24 h. In some embodiments of the present disclosure, the curing is conducted in a stainless steel mold. In an embodiment of the present disclosure, the vacuum drying is conducted at 60° C., and the vacuum drying is conducted for 24 h.

In some embodiments of the present disclosure, the melt extrusion is conducted at a die temperature of 190° C. to 210° C., preferably 195° C. to 205° C., and more preferably 198° C. to 200° C.; and the melt extrusion is conducted at a screw speed of 12 r/min to 17 r/min, preferably 13 r/min to 16 r/min, and more preferably 14 r/min to 15 r/min. In an embodiment of the present disclosure, the melt extrusion is conducted at a die temperature of 200° C., and the melt extrusion is conducted at a screw speed of 16 r/min.

In some embodiments of the present disclosure, a mass ratio of GO to PLA in the 3D-printable GO/PLA composite wire is in a range of (0.001-0.0025):1, preferably (0.0012-0.002):1, and more preferably (0.0014-0.0016):1. In an embodiment of the present disclosure, the mass ratio of the GO to the PLA in the 3D-printable GO/PLA composite wire is 0.002:1, 0.0015:1, or 0.0025:1.

In the present disclosure, after obtaining the 3D-printable GO/PLA composite wire, the 3D-printable GO/PLA composite wire is subjected to 3D printing to obtain a scaffold.

There is no special limitation on the 3D printing process, and the printing can be conducted according to design parameters of the target scaffold using a process well known to those skilled in the art.

In the present disclosure, after obtaining the scaffold, the scaffold is annealed to obtain the scaffold composite.

In some embodiments of the present disclosure, the annealing is conducted in an oven; the annealing is conducted at an oven temperature of 100° C. to 140° C., preferably 110° C. to 130° C., and more preferably 118° C. to 122° C.; the annealing is conducted for 30 min to 90 min, preferably 40 min to 80 min, and more preferably 50 min to 70 min. In an embodiment of the present disclosure, the annealing is conducted at 120° C., and the annealing is conducted for 2 h. In the present disclosure, the effect of the annealing is to release a residual stress, thereby improving the stability and mechanical properties of the scaffold material.

The present disclosure further provides a scaffold composite prepared by the preparation method as described above.

The present disclosure further provides use of the scaffold composite as described above in preparation of a medical implant material. In some embodiments of the present disclosure, the medical implant material is a spinal scaffold material. There is no special limitation on the use method, and the methods well known to those skilled in the art can be used.

The scaffold composite, and the preparation method and use thereof provided by the present disclosure will be described in detail with reference with the following examples, but they should not be construed as limiting the scope of the present disclosure.

Example 1

10 mg of GO and 8 mL of DMF were mixed under an ultrasonic treatment (at a frequency of 40 kHz for 120 min) to obtain a GO dispersion (with a mass concentration of 0.131 wt %).

5 g of PLA was added into 130 mL of DMF, and mixed under stirring (at 30° C. for 120 min) to obtain a PLA dispersion (with a mass concentration of 3.915 wt %).

The GO dispersion was slowly added into the PLA dispersion at a speed of 4 mL/min, then stirred (at 30° C. for 60 min), and subjected to curing by vacuum drying (at 60° C. for 24 h), and melt extrusion (at a die temperature of 200° C. and a screw speed of 16 r/min) in sequence to obtain a 3D-printable GO/PLA composite wire.

The 3D-printable GO/PLA composite wire was placed in a 3D printer according to design parameters of a spinal scaffold, subjected to 3D printing, and then dried at 120° C. for 2 h to obtain a spinal scaffold composite.

The spinal scaffold composite was subjected to mechanical performance testing, which was conducted as follows: in accordance with the requirements of ASTM D638, a tensile testing machine was used to test the tensile properties of the samples. Testing condition included room temperature (25° C.) and a loading rate of 5 mm/min. The test results show a tensile strength of 3.2 MPa.

The spinal scaffold composite was subjected to conductive performance testing, which was conducted as follows: in accordance with ASTM D257, a resistance meter was used to measure the resistivity of the samples. Testing condition included room temperature (25° C.). The test results show a conductivity of 50 S/m.

The spinal scaffold composite was subjected to antibacterial performance testing, which was conducted as follows or referred to a testing standard as follows: in accordance with ASTM E2180, the antibacterial properties of the samples were evaluated. Test bacteria included *Escherichia coli* and *Staphylococcus aureus*. The test results show an antibacterial rate of 99.3%.

Cytotoxicity testing of the spinal scaffold composite was conducted as follows: in accordance with the requirements of ISO 10993-5, cell cultures and cell lines were used to evaluate the cytotoxicity of materials by the direct contact method. The test results show a cell viability of 75%.

Example 2

7.5 mg of GO and 7 mL of DMF were mixed under an ultrasonic treatment (at a frequency of 40 kHz for 120 min) to obtain a GO dispersion (with a mass concentration of 0.113 wt %).

5 g of PLA was added into 130 mL of DMF, and mixed under stirring (at 30° C. for 120 min) to obtain a PLA dispersion (with a mass concentration of 3.915 wt %).

The GO dispersion was slowly added into the PLA dispersion at a speed of 4 mL/min, then stirred (at 30° C. for 60 min), and subjected to curing by vacuum drying (at 60° C. for 24 h), and melt extrusion (at a die temperature of 200° C. and a screw speed of 16 r/min) in sequence to obtain a 3D-printable GO/PLA composite wire.

The 3D-printable GO/PLA composite wire was placed in a 3D printer according to design parameters of a spinal scaffold, subjected to 3D printing, and then dried at 120° C. for 2 h to obtain a spinal scaffold composite.

The spinal scaffold composite was subjected to mechanical performance testing, which was conducted as follows: in accordance with the requirements of ASTM D638, a tensile testing machine was used to test the tensile properties of the samples. Testing conditions included room temperature (25° C.) and a loading rate of 5 mm/min. The test results show a tensile strength of 4.0 MPa.

The spinal scaffold composite was subjected to conductive performance testing, which was conducted as follows: in accordance with ASTM D257, a resistance meter was used to measure the resistivity of the samples. Testing condition included room temperature (such as 25° C.). The test results show a conductivity of 22 S/m.

The spinal scaffold composite was subjected to antibacterial performance testing, which was conducted as follows or referred to a testing standard as follows: in accordance with ASTM E2180, the antibacterial properties of the samples were evaluated. Test bacteria included *Escherichia coli* and *Staphylococcus aureus*. The test results show an antibacterial rate of 99.4%.

Cytotoxicity testing of the spinal scaffold composite was conducted as follows: in accordance with the requirements of ISO 10993-5, cell cultures and cell lines were used to evaluate the cytotoxicity of materials by the direct contact method. The test results show a cell viability of 78%.

Example 3

12.5 mg of GO and 8 mL of DMF were mixed under an ultrasonic treatment (at a frequency of 40 kHz for 120 min) to obtain a GO dispersion (with a mass concentration of 0.165 wt %).

5 g of PLA was added into 130 mL of DMF, and mixed under stirring (at 30° C. for 120 min) to obtain a PLA dispersion (with a mass concentration of 3.915 wt %).

The GO dispersion was slowly added into the PLA dispersion at a speed of 4 mL/min, then stirred (at 30° C. for 60 min), and subjected to curing by vacuum drying (at 60° C. for 24 h), and melt extrusion (at a die temperature of 200° C. and a screw speed of 16 r/min) in sequence to obtain a 3D-printable GO/PLA composite wire.

The 3D-printable GO/PLA composite wire was placed in a 3D printer according to design parameters of a spinal scaffold, subjected to 3D printing, and then dried at 120° C. for 2 h to obtain a spinal scaffold composite.

The spinal scaffold composite was subjected to mechanical performance testing, which was conducted as follows: in accordance with the requirements of ASTM D638, a tensile testing machine was used to test the tensile properties of the samples. Testing conditions included room temperature (25° C.) and a loading rate of 5 mm/min. The test results show a tensile strength of 3.2 MPa.

The spinal scaffold composite was subjected to conductive performance testing, which was conducted as follows:

in accordance with ASTM D257, a resistance meter was used to measure the resistivity of the samples. Testing condition included room temperature (such as 25° C.). The test results show a conductivity of 65 S/m.

The spinal scaffold composite was subjected to antibacterial performance testing, which was conducted as follows or referred to a testing standard as follows: in accordance with ASTM E2180, the antibacterial properties of the samples were evaluated. Test bacteria included *Escherichia coli* and *Staphylococcus aureus*. The test results show an antibacterial rate of 99.1%.

Cytotoxicity testing of the spinal scaffold composite was conducted as follows: in accordance with the requirements of ISO 10993-5, cell cultures and cell lines were used to evaluate the cytotoxicity of materials by the direct contact method. The test results show a cell viability of 76%.

In summary, the scaffold composite in the present disclosure achieves optimization in aspects such as mechanics, conductivity, antibiosis, and osteogenesis, and makes up for many shortcomings of existing spinal scaffolds. The scaffold composite in the present disclosure is expected to promote the progress of spinal implant technologies, benefit a greater number of patients with spinal diseases, and further enable the introduction of bionic design to achieve a better match of scaffold performance and morphology with the human spine.

The above descriptions are merely preferred embodiments of the present disclosure. It should be noted that a person of ordinary skill in the art may further make several improvements and modifications without departing from the principle of the present disclosure, but such improvements and modifications also should be deemed as falling within the scope of the present disclosure.

What is claimed is:

1. A method for preparing a scaffold composite, comprising:
    mixing a graphene oxide (GO) dispersion and a polylactic acid (PLA) dispersion, and subjecting a resulting mixed dispersion to curing and melt extrusion in sequence to obtain a 3-dimensional (3D)-printable GO/PLA composite wire;
    subjecting the 3D-printable GO/PLA composite wire to 3D printing to obtain a scaffold; and
    annealing the scaffold to obtain the scaffold composite;
    wherein the annealing is conducted in an oven;

the annealing is conducted at an oven temperature of 120° C. for 2 h;
    the melt extrusion is conducted at a screw speed of 16 rotations/minute (r/min); and
    wherein a mass ratio of GO to PLA in the 3D-printable GO/PLA composite wire is in a range of 0.001:1 to 0.0025:1.

2. The method of claim 1, wherein a solvent in the GO dispersion and a solvent in the PLA dispersion comprise independently one or more selected from the group consisting of difluoromethane, fluorobenzene, N, N-dimethylacetamide (DMAc), and N, N-dimethylformamide (DMF).

3. The method of claim 1, wherein the mixing is conducted under stirring at a temperature of 28° C. to 35° C. for 40 minutes to 80 minutes; and
    the PLA dispersion is prepared by mixing PLA with an organic solvent at a temperature of 28° C. to 35° C. for 90 minutes to 180 minutes.

4. The method of claim 1, wherein the curing is conducted by vacuum drying; and
    the vacuum drying is conducted at a temperature of 50° C. to 70° C. for 24 hours.

5. The method of claim 1, wherein the melt extrusion is conducted at a die temperature of 190° C. to 210° C.

6. A scaffold composite prepared by the method of claim 1.

7. The scaffold composite of claim 6, wherein a solvent in the GO dispersion and a solvent in the PLA dispersion comprise independently one or more selected from the group consisting of difluoromethane, fluorobenzene, N, N-dimethylacetamide (DMAc), and N, N-dimethylformamide (DMF).

8. The scaffold composite of claim 6, wherein the mixing is conducted under stirring at a temperature of 28° C. to 35° C. for 40 minutes to 80 minutes; and
    the PLA dispersion is prepared by mixing PLA with an organic solvent at a temperature of 28° C. to 35° C. for 90 minutes to 180 minutes.

9. The scaffold composite of claim 6, wherein the curing is conducted by vacuum drying; and
    the vacuum drying is conducted at a temperature of 50° C. to 70° C. for 24 hours.

10. The scaffold composite of claim 6, wherein the melt extrusion is conducted at a die temperature of 190° C. to 210° C.

* * * * *